United States Patent [19]

Wederhorn et al.

[11] Patent Number: 5,444,754
[45] Date of Patent: Aug. 22, 1995

[54] METHOD FOR LOCALIZING CROSS-SECTIONAL DENTAL X-RAY IMAGES

[75] Inventors: Markku Wederhorn, Nurmijärvi; Panu Kopsala, Tuusula, both of Finland

[73] Assignee: Instrumentarium Corp., Finland

[21] Appl. No.: 245,752

[22] Filed: May 18, 1994

Related U.S. Application Data

[63] Continuation-in-part of Ser. No. 165,731, Dec. 10, 1993, abandoned.

[30] Foreign Application Priority Data

Oct. 13, 1993 [FI] Finland .................................. 934516

[51] Int. Cl.6 .............................................. A61B 6/14
[52] U.S. Cl. ......................................... 378/38; 378/163; 378/170
[58] Field of Search ................. 378/38, 162, 163, 165, 378/168, 169, 175, 205, 170

[56] References Cited

U.S. PATENT DOCUMENTS

| | | | |
|---|---|---|---|
| 4,783,793 | 11/1988 | Virta et al. | 378/39 |
| 4,971,060 | 11/1990 | Schneider et al. | 128/653.1 |
| 5,052,035 | 9/1991 | Krupnick | 378/163 |
| 5,216,700 | 6/1993 | Cherian | 378/163 |

FOREIGN PATENT DOCUMENTS

| | | |
|---|---|---|
| 374361 | 6/1990 | European Pat. Off. |
| 499595 | 8/1992 | European Pat. Off. |
| 512964 | 11/1992 | European Pat. Off. |
| 558464 | 9/1993 | European Pat. Off. |

*Primary Examiner*—David P. Porta
*Assistant Examiner*—Don Wong
*Attorney, Agent, or Firm*—Andrus, Sceales, Starke & Sawall

[57] ABSTRACT

The invention relates to a method for localizing cross-sectional X-ray images (6) taken from a given part of the dental arch, said imaging being effected with a panoramic X-ray apparatus which is provided with a patient supporting mechanism (1) and software for imaging the jaw in the transverse direction. The method includes a step of imaging cross-sections (6) on the same film as a respective longitudinal image (5) of the dental arch, and the cross-sectional images (6) are exposed to include identifications (A, B, C) for the sections, said identifications being also exposed on the longitudinal image (5) in alignment with the cross-sections along which the images are taken.

9 Claims, 2 Drawing Sheets

METHOD FOR LOCALIZING CROSS-SECTIONAL DENTAL X-RAY IMAGES

The present invention is a continuation-in-part application of U.S. patent application Ser. No. 08/165,731, filed Dec. 10, 1993, and now abandoned.

BACKGROUND OF THE INVENTION

The present invention relates to a method for localizing cross-sectional X-ray images taken from a given part of the maxillary or mandibular arch, said imaging being effected by means of a panoramic X-ray apparatus which is provided with a patient supporting mechanism and software for imaging the jaw in the transverse direction.

Typically, cross-sectional X-ray images of the jaw have been produced either with a plane tomographic apparatus or by computer controlled tomography. Plane tomography produces sectional images, the location of which in the jaw must be estimated from the settings of the apparatus or on the basis of anatomy shown in the sectional image. There is no clear localization visible in the image. Computer controlled dental imaging programs can be used for taking a desired section of the jaw, which also provides dimensions. The price for computer controlled tomography is substantially higher than a panoramic X-ray apparatus used in the context of this invention and, in addition, the production of an image and the calculation of dimensions in a computer controlled tomographic apparatus requires the use of a computer.

SUMMARY OF THE INVENTION

An object of the present invention is to provide a relatively simple method for showing the exact location of a cross-sectional X-ray image of the jaw. Furthermore, in the method of the invention, the identification for a cross-sectional image can be provided with a vertical measuring scale.

In order to achieve the objects of the present invention, the method of the invention is characterized as including the step of imaging the cross-sections on the same film as a respective longitudinal image of the maxillary or mandibular arch, and that the sectional images are exposed to include identifications for the sections, said identifications being also exposed on the longitudinal image in alignment with the cross-sections.

The method of the invention is carried out by means of a panoramic X-ray apparatus intended for dental imaging and including a special program which, with a suitable patient positioning, produces sectional images perpendicular to the jaw. A suitable number of sectional images, i.e. 3 to 4 images, are produced on one half of the 15×30 cm film in the apparatus. Each sectional image is from a different part of the jaw, the section having a thickness of approximately 4 mm. The other end or half of the film is used for longitudinal imaging of the jaw including locations corresponding to those of the sections, whereby locations of the sections are visible in the longitudinal image. Each section is given an identification, e.g. A, B, C, which is also adapted to appear in the longitudinal image at a location corresponding to the section. The identification included in a section can be provided with a vertical measuring scale, which takes into consideration the ratio of magnification used in imaging. The method can be used for imaging sections of the jaw and for determining the location thereof by means of a longitudinal image with all information included in a single film.

BRIEF DESCRIPTION OF THE DRAWINGS

The invention will now be described with reference made to the accompanying drawings, in which.

DETAILED DESCRIPTION OF THE PREFERRED EMBODIMENT

Figure 1:
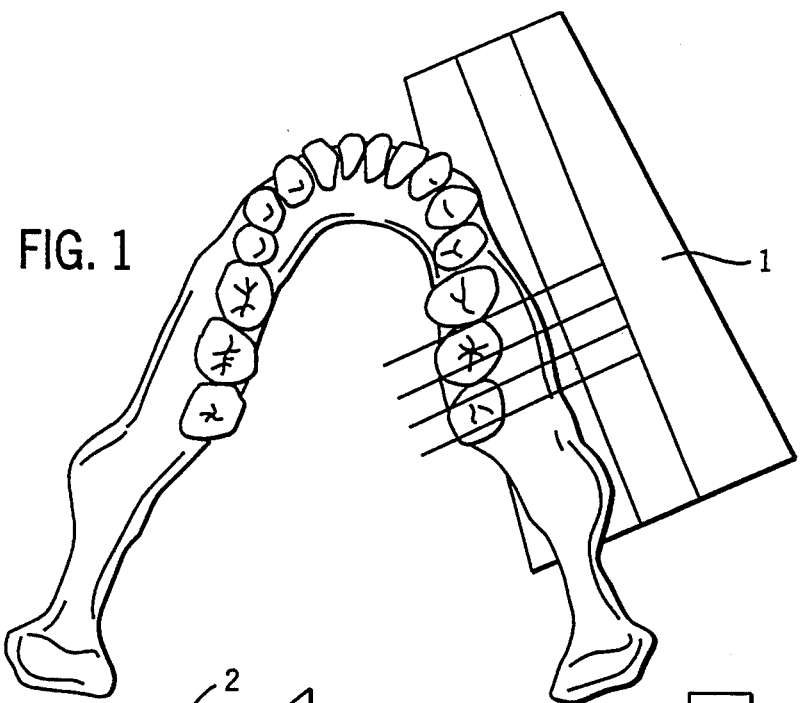
FIG. 1 shows an assembly for carrying out a method of the invention.
Figure 1A:
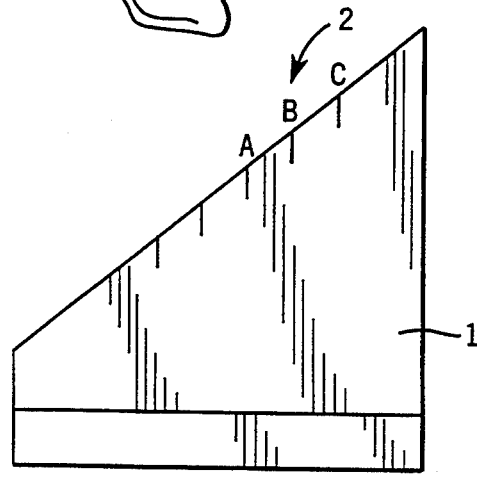
FIGS. 1a and 1b respectively illustrate in a side view and a front view a patient support for use in a method of the invention.
Figure 1B:
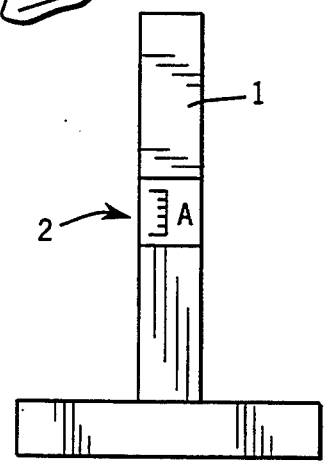

The assembly of FIG. 1 makes use of a patient support 1 in the shape of the letter T placed substantially upside down, the horizontal member of said T being placed underneath the maxilla or jawbone for guiding it vertically to a correct level. The vertical member of the T shaped assembly guides the jawbone in the horizontal plane in a manner that the image projection of lateral movement becomes correct in relation to the X-ray beam and the movement of the center of rotation of the panoramic X-ray apparatus. The identification of a section point is included in the vertical member of the T shaped assembly together with possibly also a vertical measuring scale 2 (1:1). The vertical member of the T shaped assembly rises in such a manner that the identifications of the sections lie on different levels so as not to be imaged on top of each other.

Figure 2:
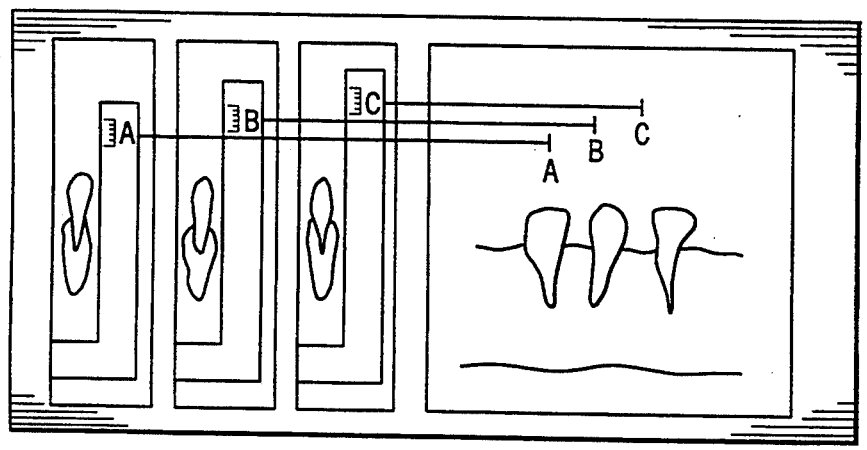
FIG. 2 shows a resulting image produced by means of the assembly of FIG. 1.

FIG. 2 illustrates a resulting image on film produced by a method of the invention. The left-hand side of the film shows three cross-sectional images with their identifications (A, B, C) together with vertical measuring scales. The right-hand side of the figure shows a longitudinal image carrying the respective identifications (A, B, C).

Figure 3:
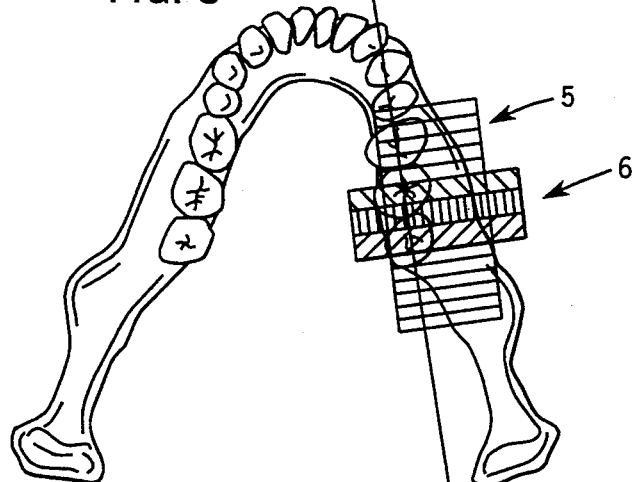
FIG. 3 shows another assembly for carrying out a method of the invention.
Figure 3A:
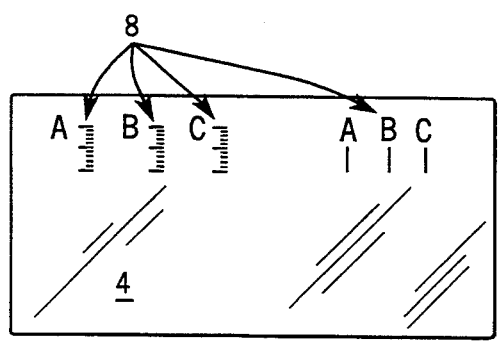
FIGS. 3a and 3b respectively illustrate elements of the assembly shown in FIG. 3.

FIGS. 3 and 3a illustrate another assembly for carrying out the method of the invention. In this assembly, the desired section point identifications are made on a transparent template 4, fitted inside a film cassette 3 and placed together with the film between reinforcement plates. The film and the template always settle at the same spot in cassette 3. During an imaging session, the reinforcement plate permits exposure of the film through template (4) except for the points of non-transparent markings, which are visible on film because the markings are unexposed. The imaging mechanics of the apparatus produces images of locations determined by the imaging program on locations in the film cassette also determined by the imaging program. Thus, the section identifications can be made in a corresponding location on a template to be inserted in the cassette. Further, a longitudinal image 5 is always imaged from a set point into a set point on the film cassette, whereby the locations of sections 6 can be marked on a template at a set point.

The imaging program images an object on a film at a set geometric ratio of magnification that can be calculated from imaging movements and mechanical dimensions of the apparatus. The imaged object enlarges from its correct or actual size by the ratio of magnification. The section identifications of the template can be provided e.g. with a millimetric scale having a pitch that differs from the correct one by the ratio of magnification. However, when the sectional image has a layer thickness of approximately 4 mm and when just vertical distances are measured, the inaccuracy resulting from a variation in the ratio of magnification is not significant.

Figure 3B:
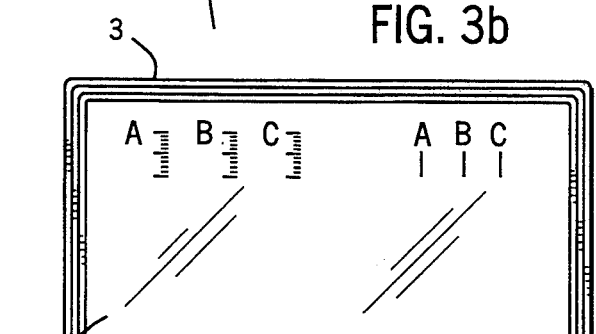

Alternatively, the markings can also be made directly on the surface of a reinforcement plate 9 as shown in FIG. 3b, whereby the reinforcement plate material covered thereby prevents exposure of the film.

Figure 4:
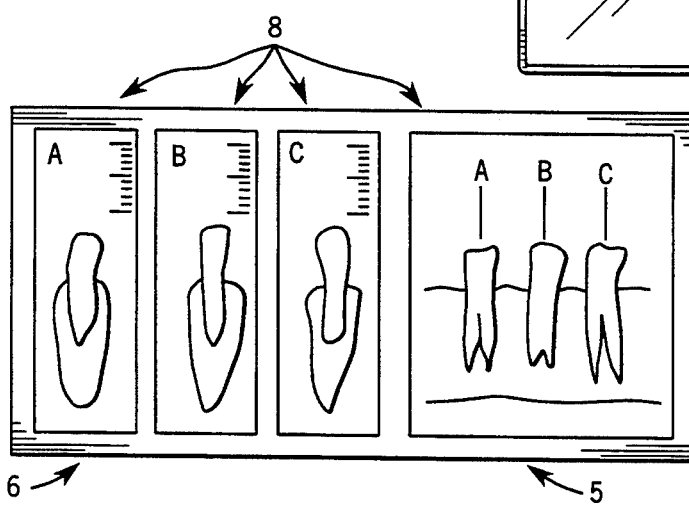
FIG. 4 shows a resulting image produced by means of the assembly of FIG. 3.

FIG. 4 shows a resulting image corresponding to FIG. 2, wherein the left-hand side of the film shows three cross-sectional images 6 and the right-hand side shows a longitudinal image 5. The film also shows markings 8 included in template 4 (sectional image identifications A, B and C as well as vertical measuring scales).

We claim:

1. A method for localizing cross-sectional images (6) taken from a given part of the maxillary or mandibular arch, said images being obtained with a panoramic X-ray apparatus which is provided with a patient supporting mechanism (1) and software for imaging the maxilla or mandible in a transverse direction, characterized in that said method includes a step of imaging cross-sections of the given part (6) on the same film as a respective longitudinal image (5) of the maxillary or mandibular arch, and that the cross-sectional images (6) are exposed to include section identifications (A, B, C) for the cross-sectional images, said section identifications being also exposed on the longitudinal image (5) in alignment with the cross-sections on which said cross-sectional images are taken.

2. A method as set forth in claim 1, characterized in that said method further comprises a step of providing at least one of the cross-sectional image (6) with a vertical measuring scale (2).

3. A method as set forth in claim 1, characterized in that a desired section identification on the film is achieved by providing a patient supporting mechanism (1) having an appropriate section identification (A, B, C) in alignment with the cross-section (6), which section identification is imaged adjacent to the cross-sectional image (6) and on the longitudinal image (5) to indicate the location of the cross-sections.

4. A method as set forth in claim 3, characterized in that said section identifications (A, B, C) for various sections included in the patient supporting mechanism (1) are positioned on different vertical levels so as not to be imaged on top of each other, the vertical levels of said section identifications indicating the location of a cross-sectional image in said longitudinal image (5).

5. A method as set forth in claim 3, characterized in that said method comprises a step of providing the patient supporting mechanism (1) not only with a section identification (A, B, C) but also with a vertical measuring scale (2), which is imaged adjacent to a cross-sectional image to facilitate the evaluation of dimensions.

6. A method as set forth in claim 1, characterized as further comprising the step of marking cross-sectional image identifications on either a reinforcing plate or transparent template of a cassette containing the film.

7. A method as set forth in claim 6, characterized as further comprising the step of marking vertical measuring scales on either a reinforcing plate or transparent template of a cassette containing the film.

8. A method as set forth in claim 2, characterized as further comprising the step of marking cross-sectional image identifications on either a reinforcing plate or transparent template of a cassette containing the film.

9. A method as set forth in claim 8, characterized as further comprising the step of marking vertical measuring scales on either a reinforcing plate or transparent template of a cassette containing the film.

* * * * *